US006051240A

United States Patent [19]
Suehara et al.

[11] Patent Number: 6,051,240
[45] Date of Patent: Apr. 18, 2000

[54] METHOD OF SEPARATING PROTECTIVE COMPONENTS OF *BORDETELLA PERTUSSIS*

[75] Inventors: Akihiro Suehara; Eiji Yamamoto; Shigeo Fujii, all of Yamaguchi, Japan

[73] Assignee: Takeda Chemical Industries, Ltd., Osaka, Japan

[21] Appl. No.: 08/530,373

[22] PCT Filed: Apr. 26, 1995

[86] PCT No.: PCT/JP95/00830

§ 371 Date: Oct. 13, 1995

§ 102(e) Date: Oct. 13, 1995

[87] PCT Pub. No.: WO95/29934

PCT Pub. Date: Nov. 9, 1995

[30] Foreign Application Priority Data

Apr. 28, 1994 [JP] Japan .................................. 6-091565

[51] Int. Cl.[7] .............................. A61K 39/10; C07K 1/00; C07K 1/14; C07K 1/36
[52] U.S. Cl. ...................... 424/240.1; 530/412; 530/414; 530/415; 530/416; 530/418
[58] Field of Search .................................. 530/412, 413, 530/414, 415, 416, 417, 418, 419, 420, 421; 424/240.1, 184.1, 234.1

[56] References Cited

U.S. PATENT DOCUMENTS

| 4,729,957 | 3/1988 | Lee et al. ................................ 435/229 |
| 4,784,589 | 11/1988 | Robinson et al. ........................... 424/9 |
| 4,849,358 | 7/1989 | Chazano et al. ......................... 435/252 |
| 5,101,014 | 3/1992 | Burns et al. ............................. 530/350 |
| 5,444,159 | 8/1995 | Jackson et al. .......................... 530/412 |

FOREIGN PATENT DOCUMENTS

| 0 047 802 | 3/1982 | European Pat. Off. . |
| 0 202 947 | 11/1986 | European Pat. Off. . |
| 0 231 083 | 8/1987 | European Pat. Off. . |
| 0 291 968 | 11/1988 | European Pat. Off. . |
| 0 336 736 | 10/1989 | European Pat. Off. . |
| 0 427 462 | 5/1991 | European Pat. Off. . |
| 0 437 687 | 7/1991 | European Pat. Off. . |
| 0 462 534 | 12/1991 | European Pat. Off. . |
| 0 484 621 | 5/1992 | European Pat. Off. . |
| WO 93/10216 | 5/1993 | WIPO . |

OTHER PUBLICATIONS

The Journal of Medical Microbiology, vol. 35, No. 3, 1991, p. 187.
Zhang et al., "Purification and Characterization of Fimbriae Isolated from *Bordetella pertussis*", Infection and Immunity, vol. 48, No. 2, May 1985, p. 422–427.
Brennan et al., "Identification of a 69–Kilodalton Nonfimbrial Protein As an Agglutinogen of *Bordetella pertussis*", Infection and Immunity, vol. 56, No. 12, Dec. 1988, p. 3189–3195.
Sato et al., "Separation and Purification of the Hemagglutinins from *Bordetella pertussis*", Infection and Immunity, vol. 41, No. 1, Jul. 1983, p. 313–320.

*Primary Examiner*—Patricia A. Duffy
*Attorney, Agent, or Firm*—Foley & Lardner

[57] ABSTRACT

To provide a method of efficiently separate protective components of *Bordetella pertussis*. On the basis of differences in adsorbability to calcium phosphate gel formed by adding calcium ions to a *Bordetella pertussis* culture in the presence of excess phosphate ions, protective components of *Bordetella pertussis* are separated from the *Bordetella pertussis* culture. Traditionally, protective components of *Bordetella pertussis* have been separated using different purification methods for the respective components. According to the present invention, the use of the same means of purification for all subject components makes it possible to purify each component with high efficiency and high recovery rate, an aspect very advantageous for industrial production. It is also possible to efficiently produce an improved purified pertussis component vaccine comprising an effective combination of pertussis filamentous hemagglutinin (FHA), pertactin (PRN, 69K-OMP), pertussis fimbriae (FIM) and pertussis toxin (PT).

43 Claims, No Drawings

METHOD OF SEPARATING PROTECTIVE COMPONENTS OF *BORDETELLA PERTUSSIS*

TECHNICAL FIELD

The present invention relates to a method of separating protective components of *Bordetella pertussis*. The pertussis component vaccine can be produced by suitably mixing the protective components separated by the method of the present invention.

BACKGROUND ART

Vaccines are widely used to prevent communicable diseases. Pertussis, a communicable respiratory disease caused by infection with *Bordetella pertussis*, is likely to severely affect patients, especially infants, due to apneic cough with occasional spasm. To cope with this disease, it has been common practice to use whole cultured cells of *Bordetella pertussis* after inactivation (inactivated vaccine). However, localized reactions at the site of vaccination and side reactions, such as fever, have been reported, creating a social urge to solve this problem. To solve this problem, there have been a large number of attempts of using protective components separated from *Bordetella pertussis* as vaccine. For example, acellular pertussis vaccine (ACP vaccine), prepared by extracting protective proteins, such as pertussis toxin (PT), pertussis filamentous hemagglutinin (FHA), pertactin (PRN, 69K-OMP) and pertussis fimbriae (FIM), from *Bordetella pertussis* cells, and removing endotoxin (ET), is being into practical application, but is not fully satisfactory, due to the drawbacks described below.

Pertussis toxin (PT), pertussis filamentous hemagglutinin (FHA), pertactin (PRN, 69K-OMP) and pertussis fimbriae (FIM), all protective components of *Bordetella pertussis* already in practical application with validated efficacy, are separated by respective methods.

Pertussis toxin (PT) can be separated by affinity chromatography using human haptoglobin as a ligand [Biochimica et Biophysica Acta, Vol. 580, p. 175 (1979)]. However, human haptoglobin can be contaminated with hepatitis virus, because it is collected from human blood; the same applies when animal sera are used. Another available method is affinity chromatography using denatured ceruloplasmin as a ligand (Japanese Patent Unexamined Publication No. 62135/1987). Although this method is free of the problem of viral contamination, some problems arise, including vaccine contamination with ceruloplasmin and the high toxicity and potential body retention of sodium thiocyanate and other eluents having protein-denaturing effect.

As for pertussis filamentous hemagglutinin (FHA), a purification method using hydroxyapatite gel is available [Infection and Immunity, Vol. 41, p. 313 (1983) and EP-A-231083, EP-A-427462, EP-A-462534; Japanese Patent Unexamined Publication Nos. 234031/1987, 169893/1992, 368337/1993). However, it takes long time for column operation, and is uneconomic due to the high cost of hydroxyapatite.

As for pertactin (PRN, 69K-OMP), affinity chromatography using a mouse serum as a ligand is available [Infection and Immunity, Vol. 56, p. 3189 (1988)], but has the same drawbacks as above.

As for pertussis fimbriae (FIM), *Bordetella pertussis* cell extract is purified by salting-out: with ammonium sulfate and magnesium chloride [Infection and Immunity, Vol. 48, p. 442 (1985)], but this method is poor in vaccine production efficiency due to low yield.

There is a method of preparing Gram-negative bacterial vaccine by adosorbing with the aluminum hydroxide gel (WO 93/10216). This method needs the large amount of the aluminum hydroxide gel, which adsorbs both the protective components and the endotoxin originated in Gram-negative bacteria. The vaccine obtained by the method of WO93/10216 has a danger of side effects, such as fever and endotoxin-shock, by the endotoxin released into body because of the diluted vaccines.

As for the pertussis vaccine production included as the components mixture without separating each protective component originated in *Bordetella pertussis*, a method of using calcium phosphate gel is available (EP-A-291968, Japanese Patent Unexamined Publication No. 52726/1989). However, this method formed the calcium phosphate in the presence of a 1M sodium chloride does not absorb the protective components.

As stated above, totally different purification methods must be used to separate the respective protective components of *Bordetella pertussis*. This approach is unsuitable to large-scale vaccine production due to painstaking operation, and difficult to apply practically. Moreover, the customary methods of separating protective components disclosed in prior art have some problems that materials or reagents have pathogenicity or toxicity.

DISCLOSURE OF INVENTION

Against the background described above, the present inventors investigated methods of efficiently separating protective components of *Bordetella pertussis*, and found that protective components of *Bordetella pertussis* can be efficiently separated from *Bordetella pertussis* culture on the basis of differences in adsorbability to calcium phosphate gel formed by adding calcium ions to the *Bordetella pertussis* culture in the presence of excess phosphate ions. The inventors made further investigation based on this finding, and the efficient and safty method of separating the protective components combined with the calcium phosphate gel treatment and elution by salt and heating was developed the present invention. Accordingly, the present invention relates to:

(1) A method of separating at least one member of the group consisting of pertussis filamentous hemagglutinin (FHA), pertactin (PRN, 69K-OMP), pertussis fimbriae (FIM), and pertussis toxin (PT) by bringing a *Bordetella pertussis* culture into contact with calcium phosphate gel which is formed by adding calcium ions to the culture in the presence of phosphate ions.

(2) A method of separating at least one member of the group consisting of pertussis filamentous hemagglutinin (FHA), pertactin (PRN, 69K-OMP), pertussis fimbriae (FIM) and pertussis toxin (PT) by separating a *Bordetella pertussis* culture into cells and culture liquid, and carrying out at least one of processes (A), (B), (C) and (D):

(A) a process in which the separated cells are eluted with a salt solution, and pertussis filamentous hemagglutinin (FHA) is separated by bringing the eluted solution into contact with calcium phosphate gel of the above item (1), (B) a process in which the cell residue resulting from the elution treatment of the above process (A) is heated in the presence of a salt solution and brought into contact with calcium phosphate gel, and pertactin (PRN, 69K-OMP) is separated by bringing the eluted solution into contact with calcium phosphate gel of the above item (1), (C) a process in which the cell residue resulting from the elution treatment of the above process (A) is heated in the presence of a salt solution, the supernatant is brought into contact with calcium phosphate gel and eluted with a salt solution, and pertussis fimbriae (FIM) is separated by bringing the eluted solution into contact with calcium phosphate gel of the above item (1), (D) a process in which the culture or the separated culture liquid is brought into contact with calcium phosphate gel of the above item (1), and pertussis toxin (PT) is separated from the supernatant.

(3) The separation method of the above item (2), wherein the supernatant is brought into contact with calcium phosphate gel and eluted with a salt solution to separate pertussis filamentous hemagglutinin (FHA) in process (A).

(4) The separation method of the above item (2), wherein the supernatant after being brought into contact with calcium phosphate gel is brought into contact with ion exchange gel to separate pertactin (PRN, 69K-OMP) in process (B).

(5) The separation method of the above item (2), wherein the supernatant is brought into contact with calcium phosphate gel and removed, and the resulting residue is eluted with a salt solution to separate pertussis fimbriae (FIM) in process (C).

(6) The separation method of the above item (2), wherein the supernatant is brought into contact with ion exchange gel to separate pertussis toxin (PT) in process (D).

(7) The separation method of the above item (2), wherein the salt solution used in processes (A) and (C) is a buffer containing an alkali metal salt.

(8) The separation method of the above item (7), wherein the salt solution is a buffer containing 0.01–1.0 M sodium chloride.

(9) The separation method of the above item (1) or (2), wherein the calcium phosphate gel is formed by adding calcium ions to the culture or the supernatant of pH 7–9 in the presence of phosphate ions.

(10) The separation method of the above item (9), wherein the equivalent ratio of phosphate ions and calcium ions is 1.25–30 equivalents of phosphate ions per equivalent of calcium ions.

(11) The separation method of the above item (9), wherein the calcium phosphate gel is formed by adding calcium acetate, as a calcium ion source, at 0.1–2 w/v % in the presence of a 0.05–0.1 M phosphate buffer.

(12) The separation method of the above item (1) or (2), wherein at least one member of the group consisting of pertussis toxin (PT), pertussis filamentous hemagglutinin (FHA), pertactin (PRN, 69K-OMP) and pertussis fimbriae (FIM) is separated, after which endotoxin is removed by adsorption to aluminum hydroxide gel in the presence of ammonium sulfate.

(13) The separation method of the above item (1) or (2), wherein at least one member of the group consisting of pertussis toxin (PT), pertussis filamentous hemagglutinin (FHA), pertactin (PRN, 69K-OMP) and pertussis fimbriae (FIM) is separated, after which endotoxin is removed by zonal centrifugation.

(14) A pertussis vaccine wherein the components PT:FHA:FIM are admixed in a ratio of 4–6:8–10:1.

(15) A pertussis vaccine wherein the components PT:FHA:PRN:FIM are admixed in a ratio of 2–6:4–10:1–2:1.

BEST MODE FOR CARRYING OUT THE INVENTION

The *Bordetella pertussis* strain used for the present invention is not subject to limitation, as long as it is capable of producing one or more than one member of the group consisting of pertussis filamentous hemagglutinin (FHA), pertactin (PRN, 69K-OMP), pertussis fimbriae (FIM) and pertussis toxin (PT), all protective components of *Bordetella pertussis*. Useful strains include known strains, such as *Bordetella pertussis* Tohama phase I strain [Infection and Immunity, Vol. 6, p. 89, (1972)] (maintained at the National Institute of Health, Ministry of Social Welfare, Tokyo, Japan (NIHJ 1052), deposited under accession number IFO 14073 at the Institute for Fermentation, Osaka since Aug. 13, 1980), *Bordetella pertussis* Yamaguchi phase I strain, *Bordetella pertussis* phase I strain 18-323 and *Bordetella pertussis* phase I strain 165, with preference given to *Bordetella pertussis* Tohama phase I strain (IFO 14073) from the viewpoint of productivity. *Bordetella pertussis* can be cultured by known methods. Useful media include known basal media, such as Cohen-Wheeler medium, Stainer-Scholte medium and other liquid media, with preference given to Stainer-Scholte medium. The solution containing protective components and endotoxin (ET) may be a culture obtained by stationary culture or tank culture. In the present invention, the culture means cultured cells or culture liquid resulting from incubating said *Bordetella pertussis*. And the present invention, the supernatant means the culture liquid or the supernatant resulting from heating the cells in the presence of a salt solution or eluting with a salt solution from the calcium phosphate gel adsorbed the protective components as described below. The cells include the culture cells and the cell residue. In the present invention, the method used to separate a *Bordetella pertussis* culture into cells and culture supernatant may be a known method, such as centrifugation or filtration.

The calcium phosphate gel used for the present invention is not a ready-made gel, but preferably calcium phosphate gel formed in a culture or a supernatant to be treated by adding calcium ions to them in the presence of excess phosphate ions (may referred to as the in-side gel forming method). Although prepared calcium phosphate gel (e.g., commercially available hydroxyapatite gel). In comparison with the former method by using the ready-made hydroxyapatite gel mentioned above (may referred to as the out-side gel forming method), the present method by using calcium phosphate gel is higher in both adsorption efficiency for pertussis filamentous hemagglutinin (FHA) and pertussis fimbriae (FIM) and recovery efficiency of them, as shown hereafter. Moreover, the calcium phosphate gel used in the present invention is better in operational efficiency because of the absence of gel pretreatment and regeneration process, and more advantageous in cost. Furthermore, each of protective components of *Bordetella pertussis* can be selectively absorbed to the calcium phosphate gel by properly selecting the ratio of phosphate ions to calcium ions. If the the culture or the supernatant to be treated with calcium phosphate gel, does not contain a sufficient amount of phosphate ions, a phosphate buffer of appropriate concentration is added to provide phosphate ions before addition of calcium ions. For example, by adding 1 M phosphate buffer, the final phosphate ion concentration is adjusted to 0.02–0.2 M, preferably 0.05–0.1 M.

The calcium ion source added is exemplified by soluble calcium salts, such as calcium acetate, calcium chloride and calcium nitrate, with preference given to calcium ions derived from calcium acetate. Concerning the ratio of phosphate ions and calcium ions, it is preferable that phosphate ions be in excess, in comparison with calcium ions. The ratio can be properly selected in each case of the protective components of *Bordetella pertussis*, as mentioned hereafter.

In process (A) above, pertussis filamentous hemagglutinin (FHA) is separated as follows: After the culture liquid, i.e. the culture supernatant, is removed from a *Bordetella pertussis* culture by a known method, such as centrifugation or filtration, a one-tenth to one-twentieth volume (relative to the amount of culture broth) (corresponding to a final cell concentration of 50–100 billion cells/ml) of a salt solution is added to the cells to elute the hemagglutinin. In this case, the salt solution used is preferably a buffer supplemented with an alkali metal salt or an alkaline earth metal salt, specifically a 0.04–0.08 M phosphate buffer supplemented with a 0.25–1.0 M alkali metal salt or alkaline earth metal salt, with greater preference given to a 0.05 M phosphate buffer supplemented with a 0.5–1.0 M alkali metal salt. The alkali metal salt or alkaline earth metal salt added to the buffer is exemplified by sodium chloride, potassium chloride and magnesium chloride. For example, it is preferable to elute the hemagglutinin by adding a one-tenth to one-twentieth volume (relative to the amount of culture broth) of a 0.04–0.08 M phosphate buffer (pH 7–9) supplemented with 0.5–1.0 M sodium chloride, more preferably a 0.05 M phosphate buffer (pH 8) supplemented with 1 M sodium chloride, to the cells collected, followed by gentle stirring at 4° C. to room temperature, preferably 8–15° C., for 1–60 minutes, preferably 1–30 minutes, and standing for 1–2 days. The solution containing the eluted pertussis filamentous hemagglutinin (FHA) is then subjected to a known method, such as centrifugation or filtration, to recover the supernatant (the cell residue obtained at the same time by this treatment is used to isolate pertactin (PRN, 69K-OMP) and pertussis fimbriae (FIM)). The thus-obtained supernatant is then brought into contact with calcium phosphate gel.

Concerning the ratio of phosphate ions and calcium ions, it is preferable that phosphate ions be in excess, in comparison with calcium ions. For example, the equivalent ratio of these ions is preferably 1.25–30 equivalents, more preferably 1.5–7.5 equivalents of phosphate ions per equivalent of calcium ions. This quantitative ratio can be expressed in molar ratio as 0.8–20 M of phosphate ions to 1 M of calcium ions, more preferably 1–5 M of phosphate ions to 1 M of calcium ions. For example, to a solution (pH 7–9) containing phosphate ions at a concentration within the above-described concentration range (0.02–0.2 M, preferably 0.05–0.1 M), a calcium salt is added to a final concentration of 4–70 mM, preferably 8–50 mM (e.g., calcium acetate added to a final concentration of 0.1–0.8 w/v %, preferably 0.2–0.6 w/v %), followed by gentle reaction at 4° C. to room temperature, preferably 8–15° C., for 1 to 4 hours, preferably 1 to 2 hours, to form calcium phosphate gel.

Although pertussis filamentous hemagglutinin (FHA) is adsorbed to the calcium acetate gel added, provided that the amount of calcium phosphate gel added to a final concentration exceeding 0.8 w/v %, it is preferable to add the calcium acetate gel in an amount such that the final concentration falls within the above concentration range, for selectively adsorbing pertussis filamentous hemagglutinin (FHA) only. After completion of the reaction, the supernatant is removed by a known method, such as centrifugation or filtration; the resulting gel precipitate is collected. To this precipitate, a one-tenth to one-twentieth volume (relative to the amount of culture broth) of a salt solution is added, to, elute the pertussis filamentous hemagglutinin (FHA). In this case, the salt solution used may be the same salt solution as used to elute pertussis filamentous hemagglutinin (FHA) from the above-described cells. It is preferable to add a one-tenth to one-twentieth volume of 0.05–0.1 M phosphate buffer (pH 7–9) supplemented with 1–2 M sodium chloride, more preferably 0.1 M phosphate buffer (pH 8) supplemented with 1–1.5 M sodium chloride, to the above-described gel precipitate, followed by gentle stirring at 4° C. to room temperature for 1 to 2 hours, to elute the hemagglutinin. After completion of the stirring, the precipitate is removed by a known method, such as centrifugation or filtration, to recover pertussis filamentous hemagglutinin (FHA) in the supernatant. The supernatant, if necessary, can be concentrated and desalinized, by ammonium sulfate salting-out or using an ultrafiltration membrane. By subjecting the supernatant obtained by the above-described treatment to the aluminum hydroxide gel treatment or zonal centrifugation described below, pertussis filamentous hemagglutinin (FHA) having endotoxin selectively removed can be separated with substantially no loss.

In process (B) or (C) above, pertactin (PRN, 69K-OMP) and pertussis fimbriae (FIM) are separated as follows: The cell residue resulting from elution of the solution containing pertussis filamentous hemagglutinin (FHA) is heated in the presence of a one-tenth to one-twentieth volume (relative to the amount of culture broth) (corresponding to a final cell concentration of 500–100 billion cells/ml) of a salt solution to extract the pertactin (PRN, 69K-OMP) and pertussis fimbriae (FIM). In this case, the salt solution used may be the same as used in process (A) above. However, it is preferable to use a one-tenth to one-twentieth volume (relative to the amount of culture broth) of 0.01–0.05 M phosphate buffer (pH 7–9) supplemented with 0.15–0.25 M sodium chloride, with greater preference given to 0.01 M phosphate buffer (pH 7) supplemented with 0.15–0.25 M sodium chloride. It is preferable that heating be achieved in warm water at 40–80° C., preferably 50–60° C., for 60 to 120 minutes, preferably 80 to 90 minutes. The heated extracted pertactin (PRN, 69K-OMP) and pertussis fimbriae (FIM) are recovered in the supernatant by a known method, such as centrifugation or filtration. The thus-obtained supernatant is then brought into contact with calcium phosphate gel. In this case, calcium phosphate gel treatment can be performed in accordance with process (A) above; however, it is preferable to perform it within the following concentration range. For example, to a solution (pH 7–9) containing phosphate ions, adjusted as necessary to a final phosphate ion concentration of 0.05–0.1 M, preferably 0.1 M, by adding a 1 M phosphate buffer, or the like, a calcium salt is added to a final concentration of 40–180 mM, preferably 55–150 mM (e.g., calcium acetate added to a final concentration of 1–2 w/v %, preferably 1.3–1.7 w/v %), followed by gentle reaction at 4° C. to room temperature, preferably 8–15° C., for 1 to 4 hours, preferably 1 to 2 hours, to form calcium phosphate gel. After completion of the reaction, the resulting precipitate and supernatant are separated from each other by a known separation method, such as filtration or centrifugation, to recover pertactin (PRN, 69K-OMP) in the supernatant and pertussis fimbriae (FIM) in the gel residue, with substantially no loss.

The crudely purified pertactin (PRN, 69K-OMP) obtained by the above-described treatment can be further purified by a known method, preferably by ion exchange gel treatment; it is preferable that the crudely purified pertactin (PRN, 69K-OMP) be previously concentrated and desalinized by ammonium sulfate salting-out or using an ultrafiltration membrane. In the present invention, useful ion exchange gels include anion exchange gel and cation exchange gel, with preference given to cation exchange gel. Contact with ion exchange gel may be achieved by the column chromatography method or the batch method. By this treatment, impurities, i.e., substances other than pertactin (PRN, 69K-

OMP) in the crudely purified pertactin (PRN, 69K-OMP), are adsorbed; the effluent is collected to yield a solution containing pertactin (PRN, 69K-OMP). In the column chromatography method, the column is packed with ion exchange gel, through which the starting material, i.e., crudely purified pertactin (PRN, 69K-OMP), is passed at a flow rate of 100–500 ml/cm$^2$/hr. In the batch method, crudely purified pertactin (PRN, 69K-OMP) is placed in a container, to which ion exchange gel is added directly, followed by stirring for about 30 minutes to 3 hours, preferably about 1 hour, to adsorb impurities, i.e., substances other than pertactin (PRN, 69K-OMP). Such impurity adsorption is achieved using a buffer of a pH value of 5.0–8.0 and an electroconductivity of 100–300 umho (0.1–0.3 mS), e.g., a 0.01–0.02 M phosphate buffer (pH 5.5–6.0). By subjecting the supernatant obtained by the above-described treatment to the aluminum hydroxide gel treatment or zonal centrifugation treatment described below, pertactin (PRN, 69K-OMP) having endotoxin removed can be separated with substantially no loss.

To the gel residue containing crude pertussis fimbriae (FIM) obtained by the above-described treatment, a one-tenth to one-twentieth volume (relative to the amount of culture broth) of a salt solution is added, to elute the pertussis fimbriae (FIM). In this case as well, the salt solution may be the same as used in process (A) above. For example, it is preferable to add a one-tenth to one-twentieth volume (relative to the amount of culture broth) of a 0.05–0.1 M phosphate buffer (pH 7–9) supplemented with 1–2 M sodium chloride, preferably a 0.1 M phosphate buffer (pH 8) supplemented with 1–1.5 M sodium chloride, followed by gentle stirring at 4° C. to room temperature for 1 to 2 hours, to elute the pertussis fimbriae (FIM). After completion of the stirring, the precipitate is removed by a known method, such as centrifugation or filtration, to recover pertussis fimbriae (FIM) in the supernatant. By subjecting the supernatant obtained by the above-described treatment to the above-described aluminum hydroxide gel treatment or zonal centrifugation treatment, pertussis fimbriae (FIM) having endotoxin selectively removed can be separated with substantially no loss.

In process (D) above, pertussis toxin (PT) is separated as follows: Although a *Bordetella pertussis* culture can be used without separation into cultured cells and culture supernatant in this process, it is preferable in respect of efficiency to recover the supernatant from the *Bordetella pertussis* culture by a known method, such as centrifugation or filtration, concentrate the supernatant about 10–20 fold using an ultrafiltration membrane, or the like, and collect the supernatant by centrifugation or another method before this process. This supernatant is then brought into contact with calcium phosphate gel. In this case, calcium phosphate gel treatment can be carried out in the same manner as in process (A) above, but it is preferable to carried out this treatment within the following concentration range. For example, to a solution (pH 7–9) containing phosphate ions, adjusted as necessary to a final phosphate ion concentration of 0.05–0.1 M, preferably 0.1 M, by adding a 1 M phosphate buffer, or the like, a calcium salt is added to a final concentration of 40–180 mM, preferably 55–150 mM (e.g., calcium acetate added to a final concentration of 1–2 w/v %, preferably 1.3–1.7 w/v %), followed by gentle reaction at 4° C. to room temperature, preferably 8–15° C., for 1 to 4 hours, preferably 1 to 2 hours, to form calcium phosphate gel. After completion of the reaction, the resulting precipitate and supernatant are separated from each other by a known method, such as centrifugation or filtration, to recover pertussis toxin (PT) in the supernatant with substantially no loss. The crudely purified pertussis toxin (PT) obtained by the above-described treatment is further purified by ion exchange gel treatment; it is preferable that the crudely purified pertussis toxin (PT) be previously concentrated and desalinized by ammonium sulfate salting-out or using an ultrafiltration membrane. The ion exchange gel used here is exemplified by anion exchange gel and cation exchange gel, with preference given to cation exchange gel. Contact with ion exchange gel may be achieved by the column chromatography method or the batch method. By this treatment, pertussis toxin (PT) in the crudely purified pertussis toxin (PT) is adsorbed to the gel, followed by washing with an appropriate buffer to elute and remove impurities, after which pertussis toxin (PT) is eluted and isolated with a buffer of appropriate pH and ionic strength. In the column chromatography method, the column is packed with ion exchange gel, through which the starting material, i.e., crudely purified pertussis toxin (PT), is passed at a flow rate of 100–500 ml/cm$^2$/hr to cause toxin adsorption. In the batch method, the crudely purified pertussis toxin (PT) is placed in a container, to which ion exchange gel is added directly, followed by stirring for about 30 minutes to 3 hours, preferably about 1 hour, to cause toxin adsorption. Such adsorption of the crudely purified pertussis toxin (PT) is achieved using a buffer of a pH level of 5.0–6.0 and an electroconductivity of 100–300 umho (0.1–0.3 mS), e.g., a 0.01–0.02 M phosphate buffer (pH 5.5–6.0). Elution from the ion exchange gel to which the pertussis toxin (PT) has been adsorbed can be achieved using a buffer of a pH level of 7.0–7.5 and an electroconductivity of 1,000–2,000 umho (1–2 mS), e.g., a 0.1–0.2 M phosphate buffer (pH 7.0–7.5). By subjecting the eluate obtained by the above-described treatment to the aluminum hydroxide gel treatment or zonal centrifugation treatment described below, pertussis toxin (PT) having endotoxin selectively removed can be separated with substantially no loss.

In the present invention, the aluminum hydroxide gel treatment for endotoxin removal is carried out to adsorb only the endotoxin selectively by bringing the subject into contact with previously prepared aluminum hydroxide gel in the presence of ammonium sulfate. But, the aluminum hydroxide gel, whose amount to be used is less than one-tenth of that used in WO93/10216, hardly absorbs any amounts of protective components of *Bordetella pertussis*. It is normally preferable that this treatment be carried out after concentration by a known method, such as ammonium sulfate salting-out or an ultrafiltration membrane method. Aluminum ions useful for the previously prepared aluminum hydroxide gel include those of soluble aluminum compounds, such as aluminum sulfate and aluminum chloride, with preference given to the aluminum ions of aluminum chloride. It is preferable that aluminum hydroxide gel be prepared by adding a 2 M sodium hydroxide solution to a 25–190 mM aluminum salt solution (e.g., 0.9–4.5% aluminum chloride solution) to a pH level of 7.0–7.5, followed by gentle reaction at 4° C. to room temperature for 1 to 3 hours, to form the desired aluminum hydroxide gel. The aluminum hydroxide gel obtained by the above-described treatment is then treated to recover the resulting gel precipitate by a known method, such as filtration or centrifugation, to remove free aluminum ions after completion of the reaction. The protective component of *Bordetella pertussis* concentrated by a known method, such as ammonium sulfate salting-out, is recovered by centrifugation; the precipitate is dissolved in a 0.25 M phosphate buffer (pH 7.0–7.5) supplemented with 0.25 M sodium chloride. To this protective component of *Bordetella pertussis*, a saturated ammonium sulfate solution is added to a final concentration of 2.0–8.0 v/v %, followed by addition of previously prepared, recovered aluminum hydroxide gel to a final concentration of 0.1–1.0 mg/ml, preferably 0.2–0.5 mg/ml, and gentle reaction at 4° C. to room temperature for 30 minutes to 1 hour. After completion of the reaction, the aluminum hydroxide gel is removed by a known method, such as filtration or centrifugation, to separate the protective component of *Bordetella pertussis* having endotoxin removed, with substantially no loss.

In the present invention, zonal centrifugation treatment is carried out to remove endotoxin, and is preferably carried out after concentration by a known method, such as ammonium sulfate salting-out. Zonal centrifugation methods include sucrose density gradient centrifugation, cesium chloride density gradient centrifugation and potassium tartrate density gradient centrifugation, with preference given to sucrose density gradient centrifugation. For example, when sucrose density gradient centrifugation is carried out on a sucrose density gradient of 0–30 w/v % at an $R_{max}$ of 60,000 to 122,000 G for about 10 to 24 hours, the protective component of *Bordetella pertussis* having endotoxin removed can be separated.

PT is detoxified by using a conventional detoxification technique as described in British Journal of Experimental Pathslogy, vol. 44, p. 177, (1963). FHA, PRN and FIM may be inactivated, for example, by the method as described in Japanese Patent Unexamined Publication No. 52726/1989. An improved purified pertussis component vaccine which is superior to a known pertussis vaccine can be produced by blending in any desireded ratio of protective components of *Bordetella pertussis* obtained by the method of present invention. Namely, it's not possible to change the ratio of each component which is stable in whole cell or co-purified acellular vaccine without obtaining furified component respectively, while an antigen ratio can be chosen in the method of present invention which gives the optimal which gives the optimal response in humans as a pertussis vaccine since each component is efficiently purified in the present invention. The purified pertussis component vaccine is desirable to blend the protective components in as little amount of total protein as possible and in a way of giving more effective immunogenicity. The purified pertussis component vaccine of the present invention preferably includes all of three components, i.e. FHA, FIM and PT, and may also include other pharmaceutically acceptable components such as PRN which does not give undesired side effects.

When blending these components to produce a purified pertussis component vaccine of the present invention, the ratio of it may be examplified in Examples metioned hereinafter. The component vaccine of the present invention has a PT:FHA:FIM ratio of approximate 4–6:8–10:1, preferably 5–6:8–10:1, and comprise, for example, 20–30 μg-protein/ml of PT, 40–50 μg-protein/ml of FHA and 5–10 μg-protein/ml of FIM, preferably 25–30 μg-protein/ml of PT, 40–50 μg-protein/ml of FHA and 5 μg-protein/ml of FIM. The component vaccine mentioned above may further include 5–10 μg-protein/ml of PRN, and has a PT:FHA:PRN:PT ratio of 2–6:4–10:1–2:1, preferably 5–6:8–10:2:1. Namely, it preferably comprise 25–30 μg-protein/ml of PT, 40–50 μg-protein/ml of FHA, 10 μg-protein/ml of PRN and 5 μg-protein/ml of FIM.

The above-described effect of the present invention can be summarized as follows: The method of the present invention is characterized by the use of the same means of purification for all subject protective components of *Bordetella pertussis*. This obviates the necessity of different painstaking procedures for the respective components as in prior art methods, thus permitting component purification with high efficiency and high recovery rate, an aspect very advantageous for industrial production. In addition, the endotoxin content, as determined by the Limulus test, is not more than 1 ng per 100 μg total protein, for all protective components of *Bordetella pertussis* obtained by the present invention, providing very high practical value. It is also possible to produce an improved purified pertussis component vaccine comprising an effective combination of pertussis filamentous hemagglutinin (FHA), pertactin (PRN, 69K-OMP), pertussis fimbriae (FIM) and pertussis toxin (PT).

EXAMPLES

The present invention is hereinafter described in more detail by means of, but is not limited to, the following working examples and reference examples. In the following description, pertussis toxin (PT), pertussis filamentous hemagglutinin (FHA), pertactin (PRN, 69K-OMP), pertussis fimbriae (FIM) and endotoxin are also referred to as PT, FHA, 69K-OMP, FIM and ET, respectively.

Example 1

*Bordetella pertussis* Tohama phase I strain was cultured to a final concentration of 2 billion cells/ml by Roux bottle stationary culture (450 ml, 35° C., 5 days) and tank agitating culture (40 l, 35° C., 2 days) using Stainer-Scholte medium, to yield a *Bordetella pertussis* culture.

The cell culture was concentrated to a one-tenth volume using an ultrafiltration membrane, after which it was centrifuged to separate the supernatant and cells. To the supernatant, a 1 M phosphate buffer (pH 8.0) was added to a final concentration of 0.1 M, followed by addition of an calcium acetate solution to a final concentration of 1.6 w/v % and stirring at room temperature for 1 hour. This calcium phosphate gel solution was filtered. The resulting filtrate was concentrated and desalinized to an electroconductivity of 200 umho using an ultrafiltration membrane, passed through a sulfopropyl cation exchange chromatography column (produced by Tosoh Corporation), washed with a 0.01 M phosphate buffer (pH 6.0), and eluted with a 0.1 M phosphate buffer (pH 7.0), to yield pertussis toxin (PT). Next, cells were dispersed in a one-tenth volume (relative to the amount of culture broth) of a 0.05 M phosphate buffer (pH 8.0) supplemented with 1 M sodium chloride, followed by centrifugation to yield the supernatant and cells. To the supernatant, a calcium acetate solution was added to a final concentration of 0.5 w/v %, followed by stirring at room temperature for 1 hour. This calcium phosphate gel solution was filtered; the resulting gel layer was collected. The gel layer was eluted with a 0.1 M phosphate buffer (pH 8.0) supplemented with 1 M sodium chloride to yield a solution containing pertussis filamentous hemagglutinin (FHA). Separately, cells were dispersed in a one-tenth volume (relative to the amount of culture broth) of a 0.01 M phosphate buffer (pH 7.0) supplemented with 0.15 M sodium chloride, after which it was heated in 60° C. warm water for 90 minutes, followed by centrifugation to yield the supernatant. To the supernatant, a 1 M phosphate buffer (pH 8.0) was added to a final concentration of 0.1 M, after which a calcium acetate solution was added to a final concentration of 1.6 w/v %, followed by stirring at room temperature for 1 hour. This calcium phosphate gel solution was filtered; the filtrate and the gel layer were collected. The filtrate was concentrated and desalinized to an electroconductivity of 200 umho using an ultrafiltration membrane and passed through a sulfopropyl cation exchange chromatography column (produced by Tosoh Corporation); the effluent was collected to yield a solution containing pertactin (PRN, 69K-OMP). Separately, the gel layer was eluted with a 0.1 M phosphate buffer (pH 8.0) supplemented with 1 M sodium chloride to yield a solution containing pertussis fimbriae (FIM).

Control sample was prepared as follows: Ammonium sulfate was added at 220 g per liter of culture broth, followed by sufficient stirring. After being kept standing at 4° C. for about 14 days, the mixture was centrifuged; the supernatant was discarded, and the precipitate was collected. To the precipitate thus obtained, a one-tenth volume (relative to the amount of culture broth) of a 0.05 M phosphate buffer (pH 8.0) supplemented with 1 M sodium chloride was added, followed by sufficient stirring. After being kept standing at 4° C. for 4 days, the mixture was again centrifuged; the supernatant was collected to yield a solution containing pertussis toxin (PT), pertussis filamentous hemagglutinin (FHA), pertactin (PRN, 69K-OMP) or pertussis fimbriae (FIM).

The pertussis toxin (PT), pertussis filamentous hemagglutinin (FHA), pertactin (PRN, 69K-OMP) or pertussis fimbriae (FIM) content in each sample was determined by ELISA, with purified products of pertussis toxin (PT), pertussis filamentous hemagglutinin (FHA), pertactin (PRN, 69K-OMP) and pertussis fimbriae (FIM) as references. Results are expressed in µg protein/ml unit.

Protein content determination: Protein precipitated with heated trichloroacetic acid was quantitated by the Lowry method, with bovine serum albumin (Fraction V, produced by Wako Pure Chemical Industries) as a reference. Results are expressed in µg protein/ml unit.

The results for Roux bottle culture broth and those for tank culture broth are shown in Tables 1 and 2, respectively.

TABLE 1

| Sample | Active Ingredient Protein Content (µg protein/ml) | Recovery* (%) | Total Protein Content (µg protein/ml) | Purity (%) (active ingredient protein content/total protein content) |
| --- | --- | --- | --- | --- |
| PT | 2656.8 | 90.0 | 2662.1 | 99.8 |
| FHA | 9161.7 | 85.0 | 9339.1 | 98.1 |
| FIM | 474.7 | 244.6 | 495.5 | 95.8 |
| 69K-OMP | 3683.8 | 244.6 | 3607.2 | 102.1 |

*Each figure represents a percent value relative to the control group.

TABLE 2

| Sample | Active Ingredient Protein Content (μg protein/ml) | Recovery* (%) | Total Protein Content (μg protein/ml) | Purity (%) (active ingredient protein content/total protein content) |
|---|---|---|---|---|
| PT | 3242.2 | 78.9 | 3359.8 | 96.5 |
| FHA | 9527.0 | 98.0 | 9752.9 | 97.7 |
| FIM | 675.0 | 1184.0 | 714.7 | 95.0 |
| 69K-OMP | 4333.5 | 2364.0 | 4505.1 | 96.3 |

*Each figure represents a percent value relative to the control group.

It is evident from these figures that each protective component was efficiently isolated, and that in the case of tank culture broths, pertactin (PRN, 69K-OMP) and pertussis fimbriae (FIM), both produced at low productivity in the case of Roux bottle culture broths, were recovered in large amounts.

Reference Example 1

To a control solution prepared by the method described in Example 1, calcium acetate was added to a final concentration of 0.5 w/v %, followed by stirring at room temperature for 1 hour. To the filtrate obtained by filtering this calcium solution, a half amount of a saturated ammonium sulfate solution was added; the mixture was kept standing at 4° C. for 7 days. This ammonium sulfate salting-out product was centrifuged; the resulting precipitate was collected and resuspended in a 0.025 M phosphate buffer (pH 7.0) supplemented with 0.25 M sodium chloride to yield a starting material. To this starting material, aluminum hydroxide gel, previously prepared to a final concentration of 0.4 mg/ml, was added; to the aluminum hydroxide gel recovered by centrifugation, ammonium sulfate was added to a final concentration of 0, 2, 4 or 8 w/v %, followed by gentle stirring at room temperature for 30 minutes. After completion of the reaction, the aluminum hydroxide gel was removed by centrifugation to separate the supernatant. Each supernatant was assayed for hemagglutination activity and endotoxin content by the methods described below. The results are shown in Table 3.

Determination of hemagglutination activity: After the sample was serially diluted 2 folds with a 0.01 M phosphate buffered saline, 0.6 v/v % chick immobilized red blood cells were added to cause hemagglutination. The maximum dilution rate of each sample showing hemagglutination was taken as the hemagglutinin titer HA. Determination of endotoxin (ET) content: Using *Escherichia coli* (Difico 055-B5) as a reference strain, ET content was determined by the Limulus test (Wako Pure Chemical kit). Results are expressed in ng/ml unit. It is evident from Table 3 that endotoxin can be selectively removed, without active ingredient loss, by treating the sample with previously prepared aluminum hydroxide gel in the presence of ammonium sulfate.

TABLE 3

| Amount of Ammonium Sulfate Added (w/v%) | Endotoxin Content (ng/ml) | HA Value (HAU/ml) | HA Recovery Rate* (%) |
|---|---|---|---|
| 0 | 15.8 | 16000 | 50.0 |
| 2 | 11.1 | 32000 | 100.0 |
| 4 | <9.0 | 32000 | 100.0 |
| 8 | <9.0 | 24000 | 75.0 |

*Each figure for endotoxin removal rate or HA recovery rate is a percent value relative to the pretreatment value.

Example 2

To each of pertussis toxin (PT), pertussis filamentous hemagglutinin (FHA), pertactin (PRN, 69K-OMP) and pertussis fimbriae (FIM) as obtained in Example 1, a half amount of a saturated ammonium sulfate solution was added, followed by sufficient stirring. After being kept standing at 4° C. for 1 week, the mixture was again centrifuged; the resulting precipitate was collected.

This precipitate was dissolved in a 0.025 M phosphate buffer (pH 7.0) supplemented with 0.25 M sodium chloride to yield a solution of pertussis toxin (PT), pertussis filamentous hemagglutinin (FHA), pertactin (PRN, 69K-OMP) or pertussis fimbriae (FIM). To each solution, a saturated ammonium sulfate solution was added to a final concentration of 4.0 v/v %. To this mixture, previously prepared, recovered aluminum hydroxide gel was added to a final concentration of 0.4 mg/ml, followed by gentle stirring for 30 minutes at room temperature. After completion of the reaction, the aluminum hydroxide gel was removed by centrifugation to yield pertussis toxin (PT), pertussis filamentous hemagglutinin (FHA), pertactin (PRN, 69K-OMP) and pertussis fimbriae (FIM).

Pertussis toxin (PT) content, pertussis filamentous hemagglutinin (FHA) content, pertactin (PRN, 69K-OMP) content and pertussis fimbriae (FIM) content were determined in the same manner as in Example 1; and endotoxin content, in the same manner as in Reference Example 1. The results are shown in Table 4.

TABLE 4

| Sample | Endotoxin Content (ng/100 μg protein) | Active Ingredient Protein Content μg protein/ml | Recovery Rate* (%) |
| --- | --- | --- | --- |
| PT | 0.01 | 2999.0 | 82.5 |
| FHA | 0.11 | 9060.2 | 95.1 |
| FIM | 0.54 | 478.6 | 70.9 |
| 69K-OMP | 0.08 | 3505.8 | 80.9 |

*Each figure for recovery rate represents a percent ratio relative to the pretreatment value.

It is evident from this table that endotoxin was selectively removed, with substantially no loss of any protective component, the endotoxin content per 100 μg protein/ml being not more than 1 ng/ml for all components.

Example 3

To each of pertussis toxin (PT), pertussis filamentous hemagglutinin (FHA), pertactin (PRN, 69K-OMP) and pertussis fimbriae (FIM) as obtained in Example 1, a half amount of a saturated ammonium sulfate solution was added, followed by sufficient stirring. After being kept standing at 4° C. for 1 week, the mixture was again centrifuged; the resulting precipitate was collected. This precipitate was dissolved in a 0.05 M phosphate buffer (pH 8.0) supplemented with 1 M sodium chloride, after which it was dialyzed by the tube method using a 0.05 M phosphate buffer (pH 8.0) supplemented with 1 M sodium chloride as the external fluid, to yield a solution of pertussis toxin (PT), pertussis filamentous hemagglutinin (FIA), pertactin (PRN, 69K-OMP) or pertussis fimbriae (FIM). The concentrate dialyzate was subjected to sucrose gradient density centrifugation on a sucrose density gradient of 1–30 w/w % and at an $R_{max}$ of 64,900 G for about 18; hours. After completion of the centrifugation, 34 w/w % sucrose was fed into the rotor at a low rate of rotation to collect fractions.

Pertussis toxin (PT) content, pertussis filamentous hemagglutinin (FHA) content, pertactin (PRN, 69K-OMP) content and pertussis fimbriae (FIM) content were determined in the same manner as in Example 1; and endotoxin content, in the same manner as in Reference Example 1. The results are shown in Table 5.

TABLE 5

| Sample | Endotoxin Content (ng/100 μg protein) | Active Ingredient Protein Content μg protein/ml | Recovery Rate* (%) |
| --- | --- | --- | --- |
| PT | 0.04 | 231.2 | 82.5 |
| FHA | 0.01 | 849.4 | 79.3 |

TABLE 5-continued

| Sample | Endotoxin Content (ng/100 μg protein) | Active Ingredient Protein Content μg protein/ml | Recovery Rate* (%) |
| --- | --- | --- | --- |
| FIM | 0.30 | 49.1 | 80.3 |
| 69K-OMP | 0.03 | 319.8 | 92.0 |

*Each figure for recovery rate represents a percent ratio relative to the pretreatment value.

It is evident from this table that: endotoxin was selectively removed, with substantially no loss of any protective component, the endotoxin content per 100 μg protein/ml being not more than 1 ng/ml for all components.

Example 4

To the PT as obtained in Example 3, with addition of amino acid such as Lysine, was added formalin to a final concentration of 0.4 v/v %, and after through mixing, was allowed to stand in an incubator at 39° C. for 21–35 days.

To each of FHA, 69K-OMP and FIM as obtained in Example 3, was added formaline to a final concentration of 0.4 v/v %, and after through mixing, was allowed to stand in an incubator at 39° C. for 7 days.

Each of these components as treated above was dialyzed against 4 mM phosphate buffer (pH 7.0) supplemented with 0.15M sodium chloride to yield detoxificated PT, inactivated FHA, inactivated 69K-OMP and inactivated FIM.

These detoxificated or inactivated components were blended in several ratios shown in Table 6 and 7, and followed by addition of aluminum chloride to a final concentration of 0.2 mg/ml to give a vaccine respectively.

The results for the experiments of mouse intracerebral potency with these blended vaccines, are shown in Table 6 and 7. The experiments were performed according to the method of Japanese Minimum Requirements for Biological Products (Association of Biologicals Manufactures of Japan).

TABLE 6

| Protein content of respective protective components (μg protein/ml) | | | | Mouse intracerebral potency | |
| --- | --- | --- | --- | --- | --- |
| PT | FHA | FIM | 69K-OMP | IU/ml | 50% effective dose (μg protein) |
| 10 | 40 | 0 | 0 | 10.9 | 1.06 |
| 20 | 30 | 0 | 0 | 13.4 | 0.89 |
| 20 | 40 | 0 | 0 | 11.6 | 1.18 |
| 20 | 50 | 0 | 0 | 13.6 | 1.18 |
| 20 | 80 | 0 | 0 | 12.6 | 1.81 |
| 30 | 40 | 0 | 0 | 19.3 | 0.85 |
| 40 | 40 | 0 | 0 | 18.7 | 1.04 |

TABLE 7

| Protein content of respective protective components (μg protein/ml) | | | | Mouse intracerebral potency | 50% effective dose (μg protein) |
|---|---|---|---|---|---|
| PT | FHA | FIM | 69K-OMP | IU/ml | |
| 25 | 25 | 0 | 0  | 19.5 | 1.18 |
| 25 | 25 | 5 | 0  | 26.0 | 0.98 |
| 25 | 25 | 0 | 10 | 24.1 | 1.18 |
| 25 | 25 | 5 | 10 | 19.3 | 1.60 |
| 25 | 50 | 0 | 0  | 24.1 | 1.47 |
| 25 | 50 | 5 | 0  | 22.2 | 1.70 |
| 25 | 50 | 0 | 10 | 23.7 | 1.68 |
| 25 | 50 | 5 | 10 | 24.8 | 1.71 |

It is evident from these figures that both inactivated 69K-OMP and inactivated FIM had small effects on the mouse intracerebral potency, and no significant difference were observed among the blended vaccines which contain more than 25 μg protein/ml of detoxificated PT.

Example 5

The experiment of mouse aerozol infection protecting potency were performed with the blended vaccines as obtained in Example 4. Each vaccine diluted to one-third was subcutaneously administered to 4 week-old mouse respectively with 0.2 ml of each diluted one. Four weeks later after the administration, each mouse was subjected to airway infection with 18–323 phase I strain of *Bordetella pertussis* by using the aerozol chamber, and 10 days later after the infection, the abdomen of each mouse was opened and the trachea and lung were picked out from each infected mice.

The specimen of each homoginized tissue applied to Bordet-Gengou agar. The agar was cultured at 35° C. for 5 days and the colonies of *Bordetella pertussis* were counted.

Based on the colony counts of the non-administered mice, the protective dose was calculated.

The 75% protective dose was calculated in the case of trachea, and the 50% protective dose was calculated in the case of lung. Results were expressed in μg protein.

And growth inhibitory rate was calculated in the high dose administered group. Equation of the growth inhibitory rate was as follows.

$$\text{Growth inhibitory rate (\%)} = \left(1 - \frac{\text{Colony counts of High-dose administered mice}}{\text{Colony counts of non-administered mice}}\right) \times 100$$

Results are shown in Table 8.

TABLE 8

| Protein content of respective protective components (μg protein/ml) | | | | Trachea | | Lungs | |
|---|---|---|---|---|---|---|---|
| PT | FHA | FIM | 69K-OMP | 75% Protective dose (μg protein) | Growth inhibitory rate (%) | 50% Protective dose (μg protein) | Growth inhibitory rate (%) |
| 40 | 40 | 0 | 0 | 3.75 | 97.5 | 1.00 | 89.9 |
| 20 | 80 | 0 | 0 | 4.76 | 87.7 | 1.10 | 92.6 |
| 25 | 50 | 0 | 0 | 4.14 | 89.5 | 0.96 | 89.7 |
| 25 | 50 | 5 | 0 | 1.07 | 100 | 0.49 | 100 |
| 25 | 50 | 0 | 10 | 1.74 | 100 | 0.49 | 100 |
| 25 | 50 | 5 | 10 | 0.52 | 100 | 0.26 | 100 |

It is evident from this table that both inactivated 69K-OMP and inactivated FIM ahad small effects on the mouse intracerebral potency, but they showed protective effect on the aerozol infection potency.

Test Example 1

Differences of adsorption performance between the calcium phosphate gel (In-side Gel) forming and the hydroxyapatite gel (Out-side Gel) on FHA and FIM.

Roux bottle stationary culture prepared by method described in Example 1. The cell culture was concentrated to a one-tenth volume using an ultrafiltration membrane, after which it was centrifuged to separate the supernatant (Sample a) and cells. The cells were dispersed in a one-tenth volume of 0.05 M phosphate buffer (pH 8.0) supplemented with 1 M sodium chloride and stirred well. It was kept standing at 4° C. for 4 days, followed by centrifugation to yield the eluted supernatant (Sample b) included PT, FHA, 69K-OMP and FIM.

The culture supernatant (Sample a) and eluted supernatant (Sample b) described above were treated as following 1) or 2).

1) Calcium Phosphate Gel (In-side Gel) Forming Treatment

To the samples, a 1 M phosphate buffer (pH 8) was added, followed by addition of a calcium acetate solution to a final concentration of 0.5 w/v %, 1.0 w/v % or 2.0 w/v % and gently stirred at room temperature for 1 hour, followed by centrifugation at 1000 rpm for 10 minutes to supernatant and gel residue. The eluted solution was obtained by eluting the gel residue with a 0.1 M phosphate buffer (pH 8.0) supplemented with a 1M sodium chloride.

2) Hydroxyapatite Gel (Out-side gel) treatment

Hydroxyapatite gel (produced by BDH Chemicals Ltd) was equilibrated with a 0.01M phosphate buffer (pH 8.0). The gel was added to 20 w/v %, 10 w/v % or 50 w/v % to the sample volume and gently stirred at room temperature for 1 hour, followed by centrifugation at 1000 rpm for 10 minutes to seperate supernatant from gel residue. The eluted solution was obtained by eluting the gel residue with a 0.1 M phosphate buffer (pH 8.0) supplemented with a 1M sodium chloride.

The content of FHA or FIM cotent in each sample was determined by ELISA, with FHA or FIM as the house references. The assay results are expressed in $\mu$g protein/ml unit. Protein content; Protein precipitated with heated trichloroacetic acid was quantitated by the Lowry method, with bovine serum albumin (Fraction V, produced by Wako Pure Chemical Industries) as a refference. Results are expressed in $\mu$g protein/ml unit.

Adsorption rate and recovery rate to the gel on FHA and FIM were calculated by following equations respectively.

$$\text{Adsorption rate (\%)} = \left(1 - \frac{\text{Supernatant of post-gel treatment}}{\text{Pre-gel treatment Sample}}\right) \times 100$$

$$\text{Recovery rate (\%)} = \frac{\text{Eluted solution of post-gel treatment}}{\text{Pre-gel treatment Sample}} \times 100$$

Results are shown in Table 9 and Table 10.

The calcium phosphate gel (In-side gel) strongly adsorbs both FHA and FIM, but the hydroxyapatite gel has small adsorption effect on the FIM. Also the Hydroxyapatite gel compared with the calcium phosphate gel, has less adsorption effect on the FHA and depend on the volume added.

Industrial Applicability

The method of the present invention is characterized by the use of the same means of purification for all subject protective components of *Bordetella pertussis*. Each component can therefore be purified with high efficiency and high recovery rate, an aspect very advantageous for industrial production. It is also possible to efficiently produce an improved purified pertussis component vaccine comprising an effective combination of pertussis filamentous hemagglutinin (FHA), pertactin (PRN, 69K-OMP), pertussis fimbriae (FIM) and pertussis toxin (PT).

We claim:

1. A method of separating or purifying protective components of *Bordetella pertussis* (*B. pertussis*), wherein the protective components are selected from the group consisting of pertussis filamentous hemagglutinin (FHA), pertussis toxin (PT), pertussis fimbriae (FIM) and pertactin (PRN), wherein the method comprises:

A) separating a *B. pertussis* culture into *B. pertussis* cells and culture supernatant;

B) concentrating the culture supernatant by means other than ammonium sulfate precipitation to obtain a concentrated culture supernatant;

C) contacting the concentrated culture supernatant with calcium ions in the presence of phosphate ions to form a first calcium phosphate gel mixture;

TABLE 9 a) Culture supernatant

| | | FHA | | FIM | |
|---|---|---|---|---|---|
| | | Absorption rate (%) | Recovery rate (%) | Absorption rate (%) | Recovery rate (%) |
| Concentration of calcium acetate added (w/v %) | 0.5 | 89.7 | 69.6 | 0.0 | 0.0 |
| | 1.0 | 90.4 | 63.0 | 95.0 | 77.9 |
| | 2.0 | 89.5 | 44.4 | 94.3 | 98.4 |
| Concentration of hydrozyapatite added (w/v %) | 2.0 | 25.4 | 27.5 | 0.0 | 0.0 |
| | 10.0 | 49.5 | 26.4 | 7.9 | 4.1 |
| | 50.0 | 90.8 | 48.9 | 22.1 | 5.3 |

TABLE 10 b) The eluted solution from the cell with 0.05M phosphate buffer (pH 8.0) supplemented with 1M-NaCl

| | | FHA | | FIM | |
|---|---|---|---|---|---|
| | | Absorption rate (%) | Recovery rate (%) | Absorption rate (%) | Recovery rate (%) |
| Concentration of calcium acetate added (w/v %) | 0.5 | 96.3 | 87.2 | 18.7 | 12.5 |
| | 1.0 | 98.7 | 61.0 | 98.8 | 74.3 |
| | 2.0 | 98.7 | 55.1 | 99.8 | 94.3 |
| Concentration of hydrozyapatite added (w/v %) | 2.0 | 10.8 | 1.0 | 4.6 | 1.1 |
| | 10.0 | 4.7 | 3.8 | 9.7 | 3.9 |
| | 50.0 | 15.6 | 16.7 | 13.5 | 8.2 |

D) separating the first calcium phosphate gel from the mixture to recover a supernatant containing a crudely purified PT;

E) contacting the supernatant that contains crudely purified PT with an ion exchange gel;

F) recovering PT from an elution solution of said ion exchange gel to obtain PT free of FHA, PRN and FIM;

G) treating the separated cells from step A with a salt solution to form a cell extract;

H) separating the cell extract into an extracted supernatant fraction and a cell residue fraction;

I) contacting the extracted supernatant fraction with calcium ions in the presence of phosphate ions to form a second calcium phosphate gel mixture; and J) separating the second calcium phosphate gel from the second mixture and recovering the FHA from the second calcium phosphate gel.

2. The method according to claim 1, further comprising:

K) heating the cell residue fraction of step H and extracting said cell residue with a salt solution to obtain a supernatant;

L) contacting the supernatant from step K with calcium ions in the presence of phosphate ions to form a third calcium phosphate gel mixture;

M) separating the third calcium phosphate gel mixture into a calcium phosphate gel fraction and a supernatant; and N) recovering the FIM from the third calcium phosphate gel and the PRN from the separated supernatant of step M.

3. The method according to claim 1, wherein the recovering of FHA comprises separating the FHA from the second calcium phosphate gel of step J by elution with a salt solution to obtain a liquid containing FHA.

4. The method according to claim 2, wherein the recovering of FIM comprises eluting the FIM from the third calcium phosphate gel of step N with a salt solution and recovering the FIM in the elution supernatant.

5. The method according to claim 2, wherein at least one of the calcium phosphate gel is formed at a pH in the range of 7 to 9.

6. The method according to claim 2, wherein the equivalent ratio of phosphate ions and calcium ions is 1.25 to 30 equivalents of phosphate ions per equivalent of calcium ions.

7. The method according to claim 1, wherein at least one of the calcium phosphate gel is formed by adding calcium acetate, as a calcium ion source, at 0.1 to 2 w/v % in the presence of a 0.05 to 0.1 M phosphate buffer.

8. The method according to claim 7, wherein said calcium phosphate gel is the first calcium phosphate gel formed in step C and said calcium acetate is added to a final concentration of 1 to 2 w/v %.

9. The method according to claim 8, wherein said calcium acetate is added to a final concentration of 1.3 to 1.7 w/v %.

10. The method according to claim 7, wherein said calcium phosphate gel is the second calcium phosphate gel formed in step I and said calcium acetate is added to a final concentration of 0.1 to 0.8 w/v %.

11. The method according to claim 10, wherein said calcium acetate is added to a final concentration of 0.2 to 0.6 w/v %.

12. The method according to claim 2, wherein at least one of the calcium phosphate gel is formed by adding calcium acetate, as a calcium ion source, at 0.1 to 2 w/v % in the presence of a 0.05 to 0.1 M phosphate buffer.

13. The method according to claim 12, wherein said calcium phosphate gel is the third calcium phosphate gel formed in step L and said calcium acetate is added to a final concentration of 1 to 2 w/v %.

14. The method according to claim 13, wherein said calcium acetate is added to a final concentration of 1.3 to 1.7 w/v %.

15. The method according to claim 1, wherein said step B) concentration means comprises mechanical means.

16. The method according to claim 15, wherein said mechanical means comprises filtration or centrifugation.

17. The method according to claim 1, wherein said step B) concentration means comprises ultrafiltration.

18. A method of separating or purifying a protective component of *Bordetella pertussis* (*B. pertussis*), wherein the separated protective component is pertussis toxin (PT) and the method comprises:

A) separating a *B. pertussis* culture into *B. pertussis* cells and culture supernatant;

B) concentrating the culture supernatant by means other than ammonium sulfate precipitation to obtain a concentrated culture supernatant;

C) contacting the concentrated culture supernatant with calcium ions in the presence of phosphate ions to form a calcium phosphate gel mixture;

D) separating the calcium phosphate gel from the mixture to recover a supernatant containing a crudely purified PT;

E) contacting the supernatant that contains crudely purified PT with an ion exchange gel; and F) recovering PT from an elution solution of said ion exchange gel to obtain PT free of FHA, PRN and FIM.

19. The method according to claim 18, wherein the calcium phosphate gel is formed at a pH in the range of 7 to 9.

20. The method according to claim 18, wherein the equivalent ratio of phosphate ions and calcium ions is 1.25 to 30 equivalents of phosphate ions per equivalent of calcium ions.

21. The method according to claim 18, wherein the calcium phosphate gel is formed by adding calcium acetate, as a calcium ion source, at 0.1 to 2 w/v % in the presence of a 0.05 to 0.1 M phosphate buffer.

22. The method according to claim 21, wherein said calcium acetate is added to a final concentration of 1 to 2 w/v %.

23. The method according to claim 22, wherein said calcium acetate is added to a final concentration of 1.3 to 1.7 w/v %.

24. The method according to claim 18, wherein said step B) concentration means comprises mechanical means.

25. The method according to claim 24, wherein said mechanical means comprises filtration or centrifugation.

26. The method according to claim 18, wherein said step B) concentration means comprises ultrafiltration.

27. A method of separating or purifying a protective component of *Bordetella pertussis* (*B. pertussis*), wherein the separated protective component is pertussis filamentous hemagglutinin (FHA) and the method comprises:

A) separating a *B. pertussis* culture into *B. pertussis* cells and culture supernatant;

B) treating the separated cells with a salt solution to form a cell extract;

C) separating the cell extract into an extracted supernatant fraction and a cell residue fraction;

D) contacting the extracted supernatant fraction with calcium ions in the presence of phosphate ions to form a calcium phosphate gel mixture;

E) separating the calcium phosphate gel from the mixture; and

F) recovering the FHA from the calcium phosphate gel.

28. The method according to claim 27, wherein the recovering of FHA comprises separating the FHA from the calcium phosphate gel by elution with a salt solution to obtain a liquid containing FHA.

29. The method according to claim 27, wherein the calcium phosphate gel is formed at a pH in the range of 7 to 9.

30. The method according to claim 27, wherein the equivalent ratio of phosphate ions and calcium ions is 1.25 to 30 equivalents of phosphate ions per equivalent of calcium ions.

31. The method according to claim 27, wherein the calcium phosphate gel is formed by adding calcium acetate, as a calcium ion source, at 0.1 to 2 w/v % in the presence of a 0.05 to 0.1 M phosphate buffer.

32. The method according to claim 31, wherein said calcium acetate is added to a final concentration of 0.1 to 0.8 w/v %.

33. The method according to claim 32, wherein said calcium acetate is added to a final concentration of 0.2 to 0.6 w/v %.

34. A method of separating or purifying protective components of *Bordetella pertussis* (*B. pertussis*), wherein the separated protective component is pertussis fimbriae (FIM) or pertactin (PRN) and the method comprises:

A) separating a *B. pertussis* culture into *B. pertussis* cells and culture supernatant;

B) treating the separated cells with a salt solution to form a cell extract;

C) separating the cell extract into an extracted supernatant fraction and a cell residue fraction;

D) heating the cell residue in the presence of a salt solution to obtain a supernatant;

E) contacting the supernatant from step D with calcium ions in the presence of phosphate ions to form a calcium phosphate gel mixture;

F) separating the calcium phosphate gel mixture into a calcium phosphate gel fraction and a supernatant; and G) recovering the FIM from the calcium phosphate gel and the PRN from the separated supernatant of step F.

35. The method according to claim 34, wherein the recovering of FIM comprises eluting the FIM from the calcium phosphate gel with a salt solution and recovering the FIM in the elution supernatant.

36. The method according to claim 35, wherein the salt solution is a buffer containing 0.01 to 1.0 M sodium chloride.

37. The method according to claim 34, wherein the calcium phosphate gel is formed at a pH in the range of 7 to 9.

38. The method according to claim 34, wherein the equivalent ratio of phosphate ions and calcium ions is 1.25 to 30 equivalents of phosphate ions per equivalent of calcium ions.

39. The method according to claim 34, wherein the calcium phosphate gel is formed by adding calcium acetate, as a calcium ion source, at 0.1 to 2 w/v % in the presence of a 0.05 to 0.1 M phosphate buffer.

40. The method according to claim 39, wherein said calcium acetate is added to a final concentration of 1 to 2 w/v %.

41. The method according to claim 40, wherein said calcium acetate is added to a final concentration of 1.3 to 1.7 w/v %.

42. A pertussis vaccine comprising the protective components of *Bordetella pertussis* PT:FHA:FIM admixed in a weight ratio of 5:10:1 µg protein.

43. A pertussis vaccine comprising the protective components of *Bordetella pertussis* PT:FHA:PRN:FIM admixed in a weight ratio of 5:10:2:1 µg protein.

* * * * *